United States Patent [19]

White

[11] 4,248,876
[45] Feb. 3, 1981

[54] PIPERIDINE DERIVATIVES

[75] Inventor: Alan C. White, Windsor, England

[73] Assignee: John Wyeth & Brother Ltd., Taplow, England

[21] Appl. No.: 866,311

[22] Filed: Jan. 3, 1978

[30] Foreign Application Priority Data

Jan. 8, 1977 [GB] United Kingdom ............... 00681/77
Nov. 19, 1977 [GB] United Kingdom ............... 48272/77

[51] Int. Cl.³ ................. C07D 211/42; A61K 31/445
[52] U.S. Cl. .................................... 424/267; 546/216; 546/222; 546/207; 546/219
[58] Field of Search ...................... 260/293.84, 293.81; 546/216, 222; 424/267

[56] References Cited

U.S. PATENT DOCUMENTS

| | | | |
|---|---|---|---|
| 2,997,478 | 8/1961 | Walter et al. | 546/222 |
| 3,094,463 | 6/1963 | Biel | 546/222 |
| 3,853,892 | 12/1974 | Rossi | 260/293.84 |
| 4,072,685 | 2/1978 | Nedelec et al. | 260/293.84 |

FOREIGN PATENT DOCUMENTS 960895  6/1964  United Kingdom ................ 260/293.84

OTHER PUBLICATIONS

G. Lambrecht, Arch. Pharm. (1975), vol. 308(6), pp. 459–464.
Chemical Abstracts, vol. 60, 7332f.
R. E. Bowman et al., J.C.S. Perkin I, 1972, pp. 2878–2882.
N. Dennis et al., J.C.S. Perkin I, 1976, pp. 2329–2334.
E. A. Mistryukov et al., Izv. Akad. Nauk SSSR, Ser. Khim. (1969), (12) pp. 2800–2804.
P. T. Lansbury et al., J. Amer. Chem. Soc., 1968, 90, pp. 536–537.
F. E. Ziegler et al., J. Amer. Chem. Soc., 1973, 95, pp. 7458–7464.

Primary Examiner—Norma S. MIlestone
Attorney, Agent, or Firm—Arthur E. Wilfond

[57] ABSTRACT

The invention concerns novel piperidine derivatives of the formula (I)

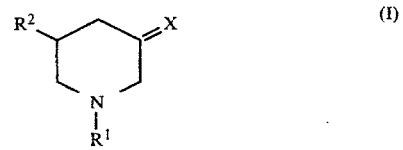

and the pharmaceutically acceptable acid addition salts thereof, wherein $R^1$ represents (lower)alkyl, $R^2$ represents a phenyl group optionally substituted by one or more (lower)alkyl, (lower)alkoxy, halogen, amino, (lower)alkylamino, di(lower)alkylamino or trifluoromethyl substituents and X represents =O;

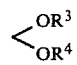

[where $R^3$ and $R^4$ both represent hydrogen, both represent the same (lower)alkyl or one is hydrogen and the other is (lower)alkyl or $R^3$ and $R^4$ together represent an alkylene group such that the

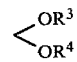

is a cyclic ketal group containing 2 or 3 carbon atoms]; or

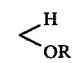

[where OR is hydroxy, etherified hydroxy or esterified hydroxy]. The compounds possess anti-depressant activity.

7 Claims, No Drawings

PIPERIDINE DERIVATIVES

This invention relates to piperidine derivatives. More particularly the invention relates to certain novel piperidine derivatives, to processes for preparing the derivatives and to pharmaceutical compositions containing them.

According to the present invention there is provided piperidine derivatives of the general formula (I)

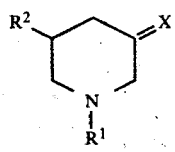

and the pharmaceutically acceptable acid addition salts thereof.

In general formula (I), $R^1$ represents (lower)alkyl, $R^2$ represents a phenyl group optionally substituted by one or more (lower)alkyl, (lower)alkoxy, halogen, amino, (lower)alkylamino, di(lower)alkylamino or trifluoromethyl substituents and X represents =O;

[where $R^3$ and $R^4$ both represent hydrogen, both represent the same (lower)alkyl or one is hydrogen and the other is (lower) alkyl or $R^3$ and $R^4$ together represent an alkylene group such that the

is a cyclic ketal group containing 2 or 3 carbon atoms]; or

[where OR is hydroxy, etherified hydroxy or esterified hydroxy].

The term "lower" as used herein to qualify a radical means that the radical contain from 1 to 6, preferably from 1 to 4 carbon atoms. By the term "halogen" is meant fluorine, chlorine or bromine.

$R^1$ can be, for example, a (lower)alkyl group such as methyl, ethyl, propyl or butyl. Preferably $R^1$ is methyl. $R^2$ can be an unsubstituted phenyl group or a phenyl group substituted by (lower)alkyl (such as methyl, ethyl, propyl or butyl), hydroxy, (lower)alkoxy (such as methoxy, ethoxy, propoxy or butoxy), halogen (e.g. chlorine or fluorine), amino, lower(alkyl)amino (e.g. methylamino), di(lower)alkylamino (e.g. dimethylamino) or trifluoromethyl.

When =X is

R can be, for example, hydrogen, lower alkyl, aryl(lower)alkyl or lower alkanoyl. The compounds in which R is hydrogen are alcohols and compounds in which R is lower alkyl (e.g. methyl, ethyl, propyl or butyl) or aryl(lower)alkyl are the corresponding ethers. When R is aryl(lower)alkyl the aryl group may be, for example, a phenyl group optionally substituted by one or more substituents such as those given in the definition of $R^2$ above. A preferred aryl(lower)alkyl group is benzyl. The compounds in which R is lower alkanoyl are esters and examples of lower alkanoyl groups are acetyl, propionyl and butyryl.

When X is =O the compounds of the invention are ketones. The ketones of the invention, although they may be prepared, are generally unstable as bases and in the form of their acid addition salts readily form their hydrates, i.e. compounds of the invention in which X is

If the acid addition salts of the ketones are crystallised from lower alkanol solvents the compounds are generally obtained in the form of their hemiketals i.e. compounds of the invention in which X is

where $R^3$ is a lower alkyl group (e.g. methyl or ethyl). These hemiketals and the ketals, i.e. compounds in which X is

where $R^3$ and $R^4$ both represent the same lower alkyl (e.g. methyl or ethyl) and compounds where

is a cyclic ketal group containing 2 or 3 carbon atoms (e.g. ethylenedioxy or 1,3-propylenedioxy), may be prepared from the ketones by methods known per se for preparing hemiketal and ketals from ketones.

The compounds of the invention in which X is =O or

may be prepared by reduction of a pyridone derivative of the general formula (II)

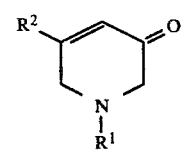

where $R^1$ and $R^2$ are as defined above or an acid addition salt thereof and, if desired, converting a free base of general formula (I) into a pharmaceutically acceptable acid addition salt thereof or converting a ketone of general formula (I) where X is =O or a pharmaceutically acceptable acid addition salt thereof into its hydrate, hemiketal or ketal.

The reduction of compounds of general formula (II) or acid addition salts thereof may be effected, for example, by catalytic hydrogenation. Suitable hydrogenation catalysts include, for example, palladium (particularly palladium on charcoal), platinum or nickel. Compounds of general formula (II) or acid addition salts thereof may also be reduced by alkali metal (e.g. lithium or sodium) in liquid ammonia.

An alternative method of preparing the compounds of the invention where X is =O or

comprises reducing a quaternary salt of the general formula (III)

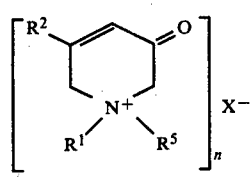

wherein $R^1$ and $R^2$ are as defined above, X is an anion of valency n (for example, a halide such as bromide) and $R^5$ is a substituent removable under the conditions of reduction and, if desired, converting a free base of general formula (I) into a pharmaceutically acceptable acid addition salt thereof or converting a ketone of general formula (I) or a pharmaceutically acceptable acid addition salt thereof into its hydrate, hemiketal or ketal.

Preferably $R^5$ is a group such as benzyl or substituted benzyl and the quaternary salts are dequaternized to the compounds of the invention by catalytic hydrogenation or reduction with alkali metal (e.g. lithium) in liquid ammonia. Alternatively $R^5$ may be a (lower)alkyl group in which case the reduction may be carried out with alkali metal in liquid ammonia. If $R^5$ is a (lower)alkyl group it is preferable that $R^1$ and $R^5$ are the same (for example, both methyl) otherwise a mixture of products may be obtained.

The pyridone starting materials of general formula (II) are known compounds or may be prepared by the process described for analogous compounds by R. E. Bowman et al, J. C. S. Perkin I, 1972, 2878–2882. For example a phenacyl bromide of general formula $$R^2COCH_2Br \qquad (IV)$$

(where $R^2$ has the meaning given above) may be condensed with a ketone of general formula (V)

$$C_6H_5CH_2NR^1CH_2COCH_3 \qquad (V)$$

(where $R^1$ has the meaning given above) to give a quaternary salt of general formula (VI)

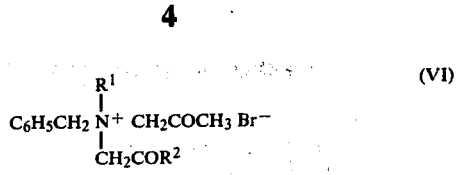

The quaternary salt (V) may be debenzylated by, for example, catalytic hydrogenation to give a diketone of general formula (VII)

$$R^2COCH_2NR^1CH_2COCH_3 \qquad (VII)$$

or an acid addition salt thereof, which may be cyclised to the compound of general formula (II) by treatment with base, e.g. with an alkali metal hydroxide or carbonate.

Starting materials of general formula (III) may be prepared by cyclising quaternary salts of general formula (VI) by a process analogous to that described by E. A. Mistryukov et al., Izv. Akad. Nauk SSSR, SEr. Khim, 1969, (12), 2800–2804. For example, the quarternary salt of general formula (VI) may be treated with a strong acid such as HBr. If the anion of the resulting quaternary compound of general formula (III) is not the one desired, the quaternary compound may be converted into the desired compound by methods known per se.

If $R^2$ in the quaternary salt of general formula (VI) is a phenyl group substituted by a lower alkoxy substituent the substituent may be cleaved by the treatment with HBr during the formation of the starting materials of general formula (III) giving compounds of general formula (III) in which $R^2$ is a phenyl group substituted by a hydroxy substituent. Similarly a compound of the invention of general formula (I) in which R is a phenyl group substituted by a (lower)alkoxy group may be cleaved to give a compound of the general formula (I) in which $R^2$ is a phenyl group substituted by a hydroxy group.

Compounds of the invention in which X is

(i.e. the alcohols) may be prepared by reducing a compound of the invention of general formula I in which X is =O or

or a pharmaceutically acceptable acid addition salt thereof with a carbonyl reducing agent.

The carbonyl reducing agent may be, for example, a hydride transfer reagent (e.g. sodium borohydride, lithium aluminium hydride, lithium tri-sec-butyl borohydride), a catalytic reducing agent (hydrogen in the presence of a catalyst such as palladium charcoal or Raney nickel) or a Meerwein-Ponndorf reducing agent. The starting material of formula (I) can be in the form of a free ketone, its hydrate, hemiketal or ketal.

Compounds of the invention in which X is

(i.e. the alcohols) may be prepared by an alternative process which comprises reducing a compound of general formula (VIII)

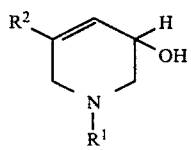
(VIII)

or a pharmaceutically acceptable acid addition salt thereof, where $R^1$ and $R^2$ have the meanings given above. The compound of formula (VIII) may, for example, be reduced by catalytic hydrogenation. The starting compound of general formula (VIII) may be prepared by reducing the compound of general formula (II) with, for example, a hydride transfer reagent (e.g. sodium borohydride).

The ethers and esters of the invention, i.e. compounds of the invention in which X is

where R is etherified or esterified hydroxy may be prepared by etherifying or esterifying the compound of the formula (I) in which X is

or its acid addition salt. The etherification or esterification of the alcohol may be carried out by the general methods known in the art for etherifying or esterifying alcohols.

If in any of the processes described above the compound of the invention is obtained as an acid addition salt, the free base can be obtained by basifying a solution of the acid addition salt although, as mentioned above, the free base of the ketone may be unstable and care may be required in its isolation. If the product of any of the processes is a free base, a pharmaceutically acceptable acid addition salt may be obtained by dissolving the free base in a suitable organic solvent and treating the solution with an acid, in accordance with conventional procedures for preparing acid addition salts from base compounds. Examples of acid addition salts are those formed from inorganic and organic acids such as sulphuric, hydrochloric, hydrobromic, phosphoric, tartaric, fumaric, maleic, citric, acetic, formic, methanesulphonic and p-toluenesulphonic acids.

The compounds of the invention possess at least one asymmetric carbon atom and hence the compounds may be, for example, in the form of optically active enantiomers or as mixtures of such enantiomers, e.g. racemates. The optical isomers may be prepared by various processes. For example, a racemic mixture of a compound of the general formula (I) may be resolved by standard methods described in the literature such as by use of an optically active acid. The racemate may be prepared by any of the processes outlined above.

The alcohols, ethers and esters of general formula (I) possess two asymmetric carbon atoms and hence the compounds can exist in various stereochemical forms all of which are provided by the invention. The ketone of general formula (I) possesses a single asymmetric carbon atom and reduction of this compound can produce an alcohol in which the OR group is cis or trans to the $R^2$ group. The proportions of the cis and trans isomers in the reduction product depend on the reducing agent used. For example we have found that use of sodium borohydride gives mainly the cis isomer and lithium tri-sec-butyl borohydride gives mainly the trans isomer. Catalytic reduction of compound VIII gives mainly the cis isomer of the alcohol of formula I.

The compounds of the present invention possess antidepressant activity as indicated by standard pharmacological procedures. In one such procedure the compounds are tested for their ability to reverse the hypothermia produced by 2.0 mg/kg reserpine administered subcutaneously to mice (Askew, Life Sciences, 1963, 1, 725–730). In this procedure it was found that cis-1-methyl-5-phenyl-3-piperidinol, a representative compound of the present invention, produced a rise in rectal temperature, compared to the control, of 9.1° C. at 20 mg/kg/p.o. while 3-methoxy-1-methyl-5-phenyl-3-piperidinol, another representative compound produced a rise in rectal temperature compared to the control of 8.3° at 10 mg/kg and 9.6° at 100 mg/kg.

The invention further provides a pharmaceutical composition which comprises a compound of general formula (I) or a pharmaceutically acceptable acid addition salt thereof, in association with a pharmaceutically acceptable carrier. The active ingredients of the compositions should, of course, be chosen so that they are stable in the particular composition employed. In the compositions of the invention the carrier may be a solid, liquid or mixture of a solid and a liquid. Solid form compositions include powders, tablets and capsules. A solid carrier can be one of more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99%, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can be dissolved in a suitable organic solvent, for instance aqueous propylene glycol containing from 10 to 75% of the glycol by weight is generally suitable.

In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from about 5 mg. to 500 mg, according to the particular need and the activity of the active ingredient. The invention also includes the compounds in the absence of carrier where the compounds are in unit dosage form. The daily dose of compound will vary depending upon the route of administration, the particular compound employed and the particular animal involved.

The following Examples illustrates the invention.

EXAMPLE 1

3-Methoxy-1-methyl-5-phenyl-3-piperidinol 1,6-Dihydro-1-methyl-5-phenyl-3(2$\underline{H}$)-pyridinone (14.0 g) in methanol (300 ml) was reduced at atmospheric pressure and ambient temperature in the presence of palladium-charcoal (10%, 1 g). Uptake of hydrogen ceased when slightly more than the theoretical quantity had been absorbed. The catalyst was filtered off and the product crystallised from the minimum quantity of methanol to give the hydrochloride of the title compound as fine colourless needles (10.07 g), m.p. 140°–42° C.

Analysis: Found C, 60.7; H, 7.9; N, 5.2; $C_{13}H_{19}NO_2HCl$ requires C, 60.6; H, 7.8; N, 5.4%).

EXAMPLE 2

3-Methoxy-1-methyl-5-phenyl-3-piperidinol (a) Phenacyl bromide (9.9 g) and benzylmethylaminoacetone (8.81 g) were dissolved in acetonitrile (25 ml) and left at room temperature for two days. The solvent was removed at reduced pressure and the gummy product triturated with ether and dried to give 19.5 g of crude quaternary compound.

The crude product (5 g) was heated in aqueous hydrobromic acid (48% 20 ml) at 96°–100° for 4 hr. The hydrobromic acid was removed under reduced pressure and re-evaporated with isopropyl alcohol (3×20 ml). The mixture was dissolved in acetone, large rhombs appeared over two days; further crystals appeared on triturating with absolute ethanol to give 1,2,3,6-tetrahydro-1-methyl-3-oxo-5-phenyl-1-(phenylmethyl)-pyridinium bromide (2.21 g) m.p. 168°–70° C.

(Analysis: Found C, 63.57; H, 5.57; N, 3.69; $C_{19}H_{20}BrNO$ requires C, 63.70; H, 5.63; N, 3.91%).

(b) The product of part (a) is hydrogenated by a procedure analogous to that of Example 1 to give the title compound.

EXAMPLE 3 cis-1-Methyl-5-phenyl-3-piperidinol

Sodium borohydride (750 mg) was added to a stirred solution of 3-methoxy-1-methyl-5-phenyl-3-piperidinol hydrochloride (2.57 g) in 96% ethanol (100 ml) and water (5 ml). After stirring for 14 hours at ambient temperature a further portion of sodium borohydride (250 mg) was added and the stirring continued for a further 3 hours. The ethanol was removed under reduced pressure and the residue dissolved with cooling in 2 N hydrochloric acid. After extraction with ether, the acid solution was made basic with 5 N sodium hydroxide solution and extracted with dichloromethane. After drying over magnesium sulphate, the solvent was removed to leave an oil which crystallised from toluene/light petroleum (b.p. 60°–80°) to afford 1.46 g of the cis isomer m.p. 125°–126° C.

(Analysis: Found, C, 76.0; H, 9.4; N, 7.1%. $C_{12}H_{17}NO$ requires C, 75.75; H, 9.0; N, 7.4%).

G.l.C. of the crude reaction mixture showed that in this reduction the ratio of cis: trans was 9:1. N.m.r. confirmed that the crystalline material had the cis configuration.

The hydrochloride of the base was prepared by dissolution in the minimum quantity of 2-propanol and addition of a solution of hydrogen chloride in dry ether. 1.28 g of the base afforded 1.2 g of hydrochloride m.p. 187°–188° C.

Analysis: Found, C, 63.6; H, 8.1; N, 6.0%. $C_{12}H_{17}NO\cdot HCl$ requires C, 63.8; H, 8.1; N, 5.7%.

EXAMPLE 4 trans-1-Methyl-5-phenyl-3-piperidinol

A suspension of 1-methyl-5-phenylpiperidin-3-one (as the hydrate hydrochloride obtained from the hemiketal of Example (1) (2.4 g) in tetrahydrofuran (THF) (20 ml) maintained at 0° C. under nitrogen was treated dropwise with a 1 M solution of lithium tri-sec-butyl borohydride (40 ml) in THF. After the addition was complete the mixture was stirred for 1 hour at ambient temperature and the solvent removed under reduced pressure. The residue was partitioned between 2 N HCl (30 ml) and ether (30 ml). The aqueous layer was basified to pH 9 with sodium carbonate and extracted with ether (3×30 ml). The combined extracts were dried over anhydrous magnesium sulphate and the solvent removed under reduced pressure. The residue was dissolved in a small volume of ethanol and treated with excess ethereal HCl. The resulting crystals were removed by filtration and recrystallised from ethanol/ether to give the title compound as the hydrochloride (1.3 g) m.p. 170°–2° C. (Analysis: Found, C, 63.0; H, 8.4; N, 5.8%. $C_{12}H_{17}NO\cdot HCl$ requires C, 63.3; H, 8.0; N, 6.2%).

EXAMPLE 5

1-Methyl-5-phenyl-3-spiro-2′-(1,3-dioxalane)piperidine

A solution of 1-methyl-5-phenylpiperidin-3-one (as the hydrate hydrochloride) (1.5 g) in ethylene glycol (15 ml) was saturated with hydrogen chloride at 0° C. The solution was heated for 1 hour at 65° C. and left overnight at ambient temperature. The reaction mixture was poured onto 50% aqueous potassium carbonate solution (30 ml) and the product extracted with ether (2×30 ml). The organic phase was washed with water (3×30 ml) and dried over anhydrous magnesium sulphate. The solution was treated with excess ethereal HCl and the resulting crystals removed by filtration. Washing with hot ether (2×50 ml) followed by drying in vacuo gave the title compound as the hydrochloride hydrate (1.4 g) m.p. 202°-4° C. (loses water at 100° C.)

Analysis: Found, C, 58.4; H, 7.55; N, 4.7%. $C_{14}H_{19}NO_2.HCl.H_2O$ requires C, 58.4; H, 7.7; N, 4.9%).

EXAMPLE 6 cis-5-(4-Chlorophenyl)-1-methyl-3-piperidinol (a) 2-(N-Acetonylmethylamino)-4-chloroacetophenone A solution of N-benzylmethylaminoacetone (17.7 g) and p-chlorophenacyl bromide (23.4 g) in acetonitrile (100 ml) was stirred for 24 hours at ambient temperature. The solvent was removed under reduced pressure and the residue triturated with ether (500 ml) to give crude quaternary bromide as a white powder (30 g).

A solution of the crude quaternary salt (29.6 g) in ethanol (200 ml) was hydrogenated over 10% palladium on charcoal in a Parr at 10 psi. After the theoretical uptake of hydrogen had occurred (c. 1.5 hour) the catalyst was removed by filtration and the filtrate evaporated under reduced pressure. The residue was recrystallised from ethanol/ether to give 2-(N-acetonylmethylamino)-4'-chloroacetophenone as the hydrobromide hemihydrate (15 g) m.p. 159°-161°.

(Analysis: Found, C, 44.0; H, 4.8; N, 4.0% $C_{12}H_{14}ClNO_2.HBr.\frac{1}{2}H_2O$ requires C, 43.7; H, 4.9; N, 4.25%).

(b) 1,6-Dihydro-1-methyl-5-(4'-chlorophenyl)-3 [2H]-pyridone

A solution of the product of Example 6a (17.6 g) in water (50 ml) was treated dropwise at 0° C. with 2 N aqueous sodium hydroxide (50 ml). The reaction mixture was stirred 15 min at ambient temperature and extracted with ether (2×100 ml). The combined organic layers were washed with saturated brine and dried over anhydrous magnesium sulphate. The ethereal solution was treated with excess ethereal HCl. The resultant oil crystallised on trituration with methanol and was recrystallised from methanol to give 1,6-dihydro-1-methyl-5-(4-chlorophenyl)-3[2H]-pyridone at the hydrochloride (1.2 g) m.p. 267°-72° C.(d).

Analysis: Found C, 55.4; H, 5.3; N, 5.7%. $C_{12}H_{13}NOCl.HCl$ requires C, 55.6; H, 5.1; N, 5.4%).

(c) 1,2,5,6-Tetrahydro-5-hydroxy-1-methyl-3-(4'-chlorophenyl)pyridine

A solution of the product of Example 6b (3.9 g) in a mixture of methanol (75 ml) and water (75 ml) was treated successively with sodium bicarbonate (1.26 g) and sodium borohydride (750 mg), with external cooling via an ice bath. After 2 hours the solvents were removed under reduced pressure and the residue partitioned between ether (100 ml) and water (100 ml). The layers were separated and the aqueous layer extracted with ether (2×100 ml). The combined organic phases were dried over anhydrous magnesium sulphate and the solvent removed under reduced pressure. Recrystallisation of the residue from cyclohexane gave 1,2,5,6-tetrahydro-5-hydroxy-1-methyl-3-]4'-chlorophenyl)-pyridine](1.5 g.) m.p. 65°-7° C.

(Analysis: Found, C, 64.3; H, 6.2; N, 6.2%. $C_{12}H_{14}NOCl$ requires C, 64.4; H, 6.3; N, 6.3%).

(d) cis-5-(4-Chlorophenyl)-1-methyl-3-piperidinol

A solution of the product of Example 6c in ethanol (50 ml) was hydrogenated over 10% Pd/C (100 mg) at ambient temperature and 1 atm pressure. After the theoretical uptake of hydrogen had occurred (c. 2 h) the catalyst was removed by filtration and the solvent removed under reduced pressure. The resulting oil was dissolved in a small volume of ethanol and treated with excess ethereal HCl. The resulting crystals were removed by filtration and recrystallised from ethanol-ether to give the title compound as the hydrochloride (550 mg) m.p. 182°-4° C.

(Analysis: Found, C, 55.15; H, 6.7; N, 5.6%. $C_{12}H_{16}ClNO.HCl$ requires C, 55.0; H, 6.5; N, 5.3%).

EXAMPLE 7 cis-3-Hydroxy-1-methyl-5-(4-methylphenyl)piperidine is prepared by an analogous method to that used in Example 6 replacing p-chlorophenacyl bromide by p-methylphenacyl bromide in Example 6(a).

EXAMPLE 8 cis-3-Methoxy-1-methyl-5-phenylpiperidine

A solution of cis-1-methyl-5-phenyl-3-piperidinol (2.03 g) in THF (20 ml) was treated with 60% sodium hydride dispersion in oil (480 mg) and heated 15 min. at reflux. The mixture was cooled to room temperature and treated with methyl tosylate (1.86 g) in THF (5 ml). The reaction mixture was stirred for 1 hour at ambient temperature, treated with water (5 ml) and the solvents removed under reduced pressure. The residue was partitioned between water (100 ml) and ether (100 ml). The organic phase was dried over magnesium sulphate and the solvent removed under reduced pressure. The resulting oil was triturated with cyclohexane (10 ml) and the resulting crystals (300 mg; unchanged starting material) removed by filtration. The mother liquors were evaporated under reduced pressure and the resulting gum converted to the fumarate which was recrystallised from methanol/ethyl acetate to give the title compound as the sesquifumarate (500 mg) Mpt. 152°-4°

Analysis: Found: C, 60.4; H, 6.6; N, 3.6% $C_{13}H_{19}NO.C_6H_6O_6$ requires: C, 60.1; H, 6.6; N, 3.7%).

EXAMPLE 9 cis-3-Benzoyloxy-1-methyl-5-phenylpiperidine

A solution of cis-1-methyl-5-phenyl-3-piperidinol (3 g.) in dichloromethane (50 ml) was treated with benzoyl chloride (2.5 ml), the resulting mixture stirred for 2 hours at ambient temperature, and the solvent then removed under reduced pressure. The residue was partitioned between ether (100 ml) and 2 N HCl. The lower two of the three layers formed were basified to pH 9 with sodium carbonate and extracted with ether (2×100 ml). The organic phase was dried (over magnesium sulphate) and treated with excess ethereal HCl. The resulting oil crystallised on trituation with methanol/ethyl acetate to give the title compound as the hydrochloride hemi-hydrate (3.1 g;) m.p. 50°.

(Found: C, 66.7; H, 7.0; N, 4.1%. $C_{19}H_{21}NO_2.HCl\frac{1}{2}H_2O$ requires: C, 67.0; H, 6.8; N, 4.1%).

EXAMPLE 10 cis-3-Acetoxy-1-methyl-5-phenylpiperidine

A solution of cis-1-methyl-5-phenyl-3-piperidinol in dichloromethane (50 ml) was treated with acetyl chloride (1.5 ml) and stirred for 2 hours. The mixture was treated with water (20 ml) and the pH adjusted to 10 with 2 N NaOH. The organic layer was dried (over magnesium sulphate) and the solvent removed under reduced pressure. The resulting oil was dissolved in ether and treated with excess ethereal HCl. The resulting crystals were removed by filtration and recrystallised from methanol/ether to give the title compound as the hydrochloride (1.9 g).

Sublimation pt. 230° C. (Found: C, 62.5; H, 7.6; N, 5.4% $C_{14}H_{19}NO_2$·HCl requires: C, 62.3; H, 7.5; N, 5.2%).

I claim:

1. A compound selected from the group consisting of a piperidine derivative of the formula

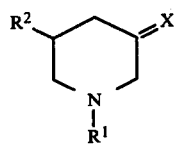

and a pharmaceutically acceptable acid addition salt thereof, wherein $R^1$ represents (lower)alkyl, $R^2$ represents a phenyl group optionally substituted by one or more sustituents selected from the group consisting of (lower)alkyl, lower(alkoxy), halogen, amino, (lower)alkylamine, di(lower)alkylamino and trifluoromethyl and X is

where OR is hydroxy, or esterified hydroxy.

2. A compound according to claim 1 which is cis-1-methyl 5-phenyl-3-piperidinol or a pharmaceutically acceptable acid addition salt thereof.

3. A compound according to claim 1 which is trans-1-methyl-5-phenyl-3-piperidinol or a pharmaceutically acceptable acid addition salt thereof.

4. A compound according to claim 1 which is cis-5-(4-chlorophenyl)-1-methyl-3-piperidinol or a pharmaceutically acceptable acid addition salt thereof.

5. A compound according to claim 1 which is cis-3-acetoxy-1-methyl-5-phenylpiperidine.

6. A compound according to claim 1 which is cis-3-benzoyloxy-1-methyl-5-phenyl piperidine.

7. A pharmaceutical composition having anti-depressant activity comprising an anti-depressant effective amount of a compound selected from the group consisting of a piperidine derivative of the formula

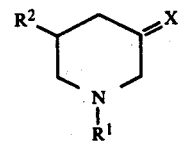

and a pharmaceutically acceptable acid addition salt thereof, wherein $R^1$ represents (lower)alkyl, $R^2$ represents a phenyl group optionally substituted by one or more substituents selected from the group consisting of (lower)alkyl, lower(alkoxy), halogen, amino, (lower)alkylamino, di(lower)alkylamino or trifluoromethyl and X is

where OR is hydroxy, or esterified hydroxy, in association with a pharmaceutically acceptable carrier.

* * * * *